United States Patent [19]

Whitehill

[11] 4,041,615

[45] Aug. 16, 1977

[54] SMALL-MOTION TEST DEVICE

[76] Inventor: Joseph Whitehill, R.D. 3 Box 278A, Chestertown, Md. 21620

[21] Appl. No.: 711,296

[22] Filed: Aug. 3, 1976

[51] Int. Cl.² .............................................. G09B 19/24
[52] U.S. Cl. ...................................... 35/13; 35/22 R; 273/1 E; 273/105.2
[58] Field of Search ................... 35/8 R, 13, 22 R, 37; 273/1 E, 105.2

[56] References Cited

U.S. PATENT DOCUMENTS

| | | | |
|---|---|---|---|
| 1,286,529 | 12/1918 | Cave | 35/8 R |
| 2,521,500 | 9/1950 | Braund | 35/22 R X |
| 2,958,956 | 11/1960 | Olalainty | 35/22 R |
| 3,029,526 | 4/1962 | Olalainty | 35/22 R |
| 3,208,747 | 9/1965 | Kavakos | 35/22 R X |
| 3,232,610 | 2/1966 | Campbell | 273/1 E |
| 3,562,927 | 2/1971 | Moskowitz | 35/37 UX |
| 3,673,708 | 7/1972 | Bevens | 35/37 |
| 3,690,020 | 9/1972 | McBratnie | 35/37 |
| 3,867,769 | 2/1975 | Schow et al. | 35/13 |
| 3,913,909 | 10/1975 | Bissell | 35/22 R X |

Primary Examiner—William H. Grieb
Attorney, Agent, or Firm—Schuyler, Birch, Swindler, McKie & Beckett

[57] ABSTRACT

A small-motion test device especially useful as a welding aptitude test and primary training device comprises a target movable along a linear track, and switch means for defining a multi-dimensional envelope of freedom of movement of said target. A wand held by the test subject must affirmatively position the target within the envelope, and maintain it there throughout the time of the test while the target moves along the track at a preprogrammed rate. Success of the test is indicated and accounted for as a function of the percentage of the total test time that the target remains within the test envelope.

10 Claims, 8 Drawing Figures

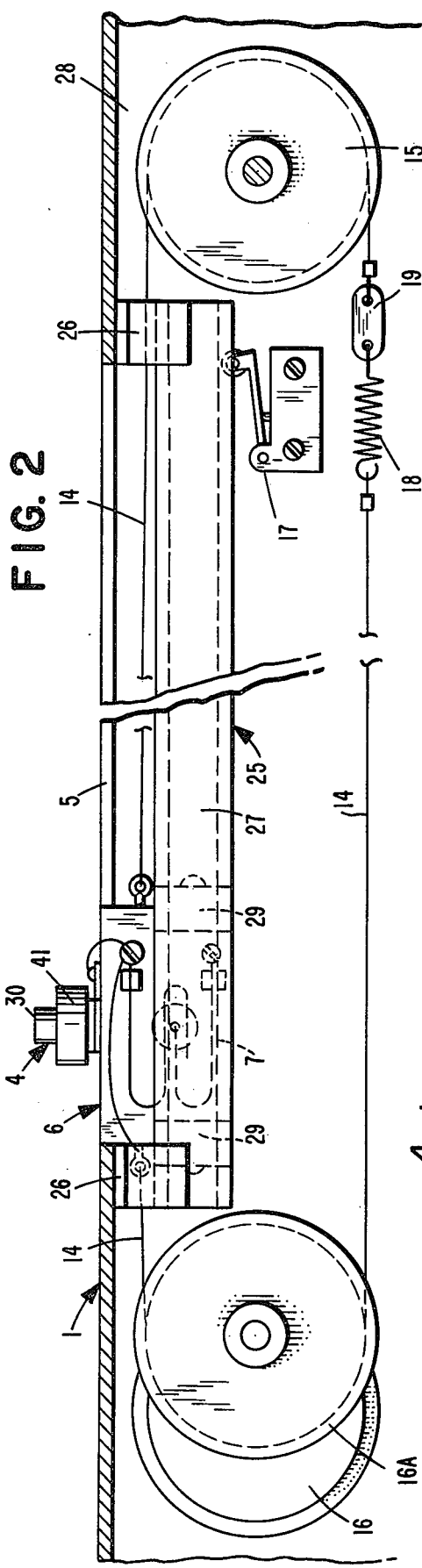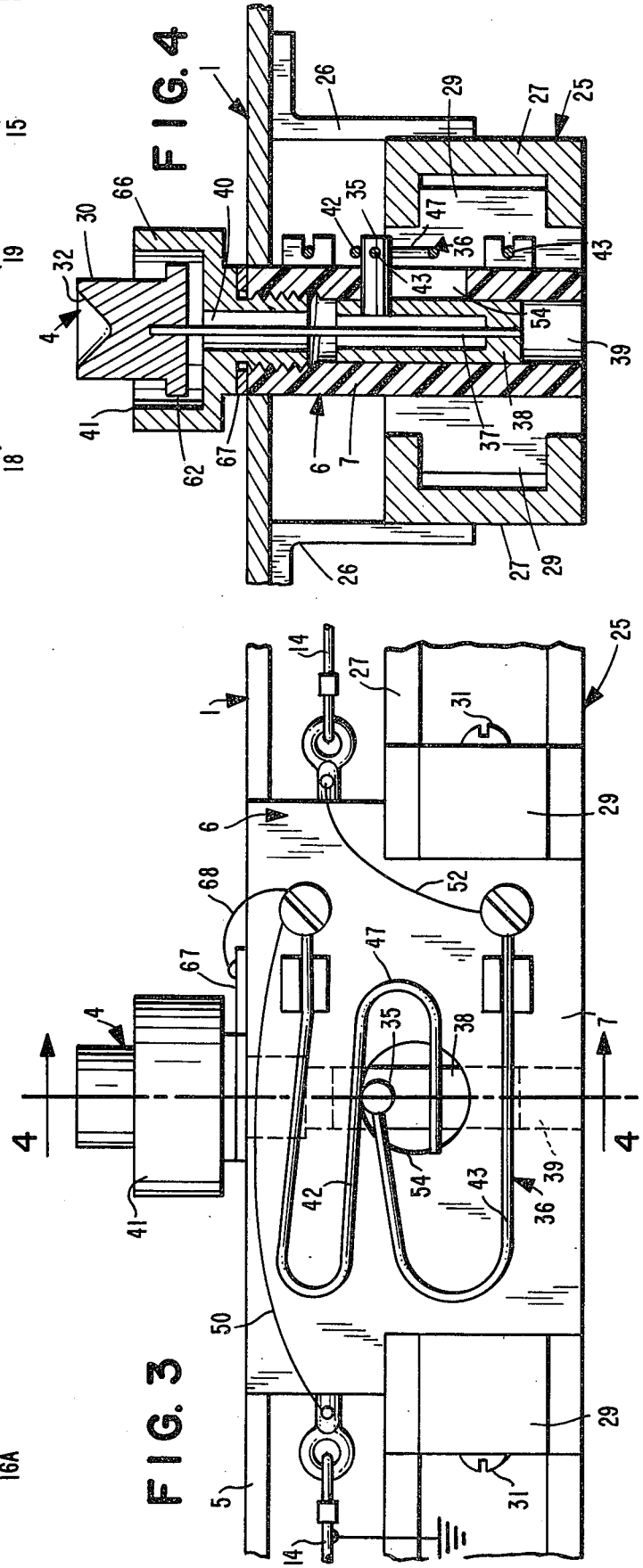

SMALL-MOTION TEST DEVICE

BACKGROUND OF THE INVENTION

1. Field of the Invention

The invention relates to the field of small-motion test apparatus.

2. Prior Art

Devices which test the ability of a subject to control limited motion have been developed in the art, both as games and for psychological testing purposes, although most such test devices have been one-dimensional. For example, Campbell U.S. Pat. No. 3,232,610 shows a magnetic target game wherein a wand must be inserted into a small aperture between magnets toward a target. Two patents to Olalainty U.S. Pat. Nos. 2,958,956, and 3,029,526 disclose psychological test apparatus wherein the user is to follow a sinuous track with a wand. Means are also provided for checking pressure of fingers on the stylus and the pressure of the stylus on the track, although only against a single upper threshold. The pressure of fingers and of the wand are checked using capacitive relays which are energized if the capacity exceeds a predetermined level. The slant of the stylus may be checked by energizing the sides of the track to detect contact with the wand.

A patent to Kavakos U.S. Pat. No. 3,208,747 shows a game wherein a stylus carrying a conductive loop is moved down a charged wire, the object being to move the loop down the wire without touching the wire. A patent to Braund U.S. Pat. No. 2,521,500 shows a system wherein a wand must be guided along a track from one end to the other within a fixed time. None of these devices utilizes an electrified target movable only within a defined envelope of freedom of movement under control of a stylus or wand as an integral part of the test apparatus. Nor do any of these earlier devices incorporate the rate at which the electrified target or wand moves as an integral part and continuing part of the test procedure; nor do any of them set upper and lower limits on the allowable vertical movement of the target. Thus as far as continuously-monitored variables are concerned, the prior art test environments are essentially one-dimensional.

The inventor is also aware of devices which move a target at a controlled rate to be followed by a wand. But as far as is known, the target itself does not carry the sensing mechanism, nor is there any control of the vertical movement of the target by the test subject, which results in a significant loss of test variables in such a prior art device. With such a device the test subject can merely follow the target with the wand he holds, rather than provide affirmative control of its orientation. Such a device is disclosed in Schow U.S. Pat. No. 3,867,769 wherein the target only carries a photocell 140 for sensing target tracking; the other test variables are monitored using switches carried on the test wand itself (FIGS. 2, 3, 4). The result is an unwieldly, unrealistic test wand of complex mechanical structure, without any simplification of the target track structure (see FIGS. 5, 6 of Schow).

Prior art small-motion devices are known which attempt to test another variable than linear motion, e.g., those patented by Olalainty, test the vertical orientation of the target achieved by the test subject by using complicated electronic means such as variable capacitance devices. Such devices are difficult to calibrate accurately and to re-use with consistent accuracy.

SUMMARY OF THE INVENTION

It is an object of this invention to provide a small-motion test device which is especially useful as a test device for muscular control in three dimensions, wherein all test circuitry is mechanically supported on the target. In such a system the wand and target may be engineered to simulate an actual working environment such as welding with great accuracy.

It is a further object of this invention to provide a small-motion test device capable of testing continuing perception and control on the part of the test subject of three simultaneous tasks, viz.: specifically positioning the tip of the wand or stylus by the test subject relative to the target in a horizontal plane parallel to the direction of target movement; specifically positioning the tip of the wand or stylus in a plane substantially perpendicular to the horizontal plane parallel to the direction of target movement; and movement of the wand with the target at the same rate of travel as the target moves under continuous automatic control. A combination of these three factors requires, for error-free passage of the test, that a test subject maintain an almost completely steady orientation of the wand in all dimensions throughout the test. Such a test device has proved to be the first successful instrument for discovering an aptitude for welding. There is a great need for welders in this country; welding training is a very popular form of vocational training and prison rehabilitation. But the training is expensive, and there are literally hundreds of applicants for each available traineeship, especially in prison-operated programs. Therefore there is a demonstrated need for a test to pinpoint special aptitude for welding among these many otherwise undistinguishable applicants. This is the first invention that has proved to be able to satisfy this need.

The test device includes a target which has a limited envelope of free movement, in both the horizontal and vertical directions. The target is electrically and mechanically coupled to a simple and reliable switch to define the envelope of freedom of movement of the target. A target drive is provided to move the target from one end of a track to the other within a fixed period of time. A wand is provided for use by the test subject; in this system, the wand is not encumbered by any switches or other structure for determining scoring on the test. The wand must be affirmatively positioned relative to the target to maintain the target within its defined envelop of freedom of movement throughout the time the test is taken. Scoring circuitry is coupled to the target switch to divide the time during which the test is taken into increments so that a score may be determined signifying the sum of the time during the test episode that the subject maintained the target within its envelope of freedom of movement. Indicating circuitry is provided both for displaying a total score based on the time the target is within the envelope and for emitting a positive signal during all the time the target is kept within the envelope during a test episode.

BRIEF DESCRIPTION OF THE DRAWINGS

FIG. 2 is a vertical, longitudinal sectional view of the test device of FIG. 1 showing especially the test drive and target.

FIG. 3 is an enlarged sectional view of a portion of FIG. 2 showing especially the switch and target of the invention.

FIG. 4 is a vertical transverse sectional view of the target shown in FIG. 3 and taken along the line 4—4 of that figure.

DETAILED DESCRIPTION OF THE PREFERRED EMBODIMENT

Figure 1:
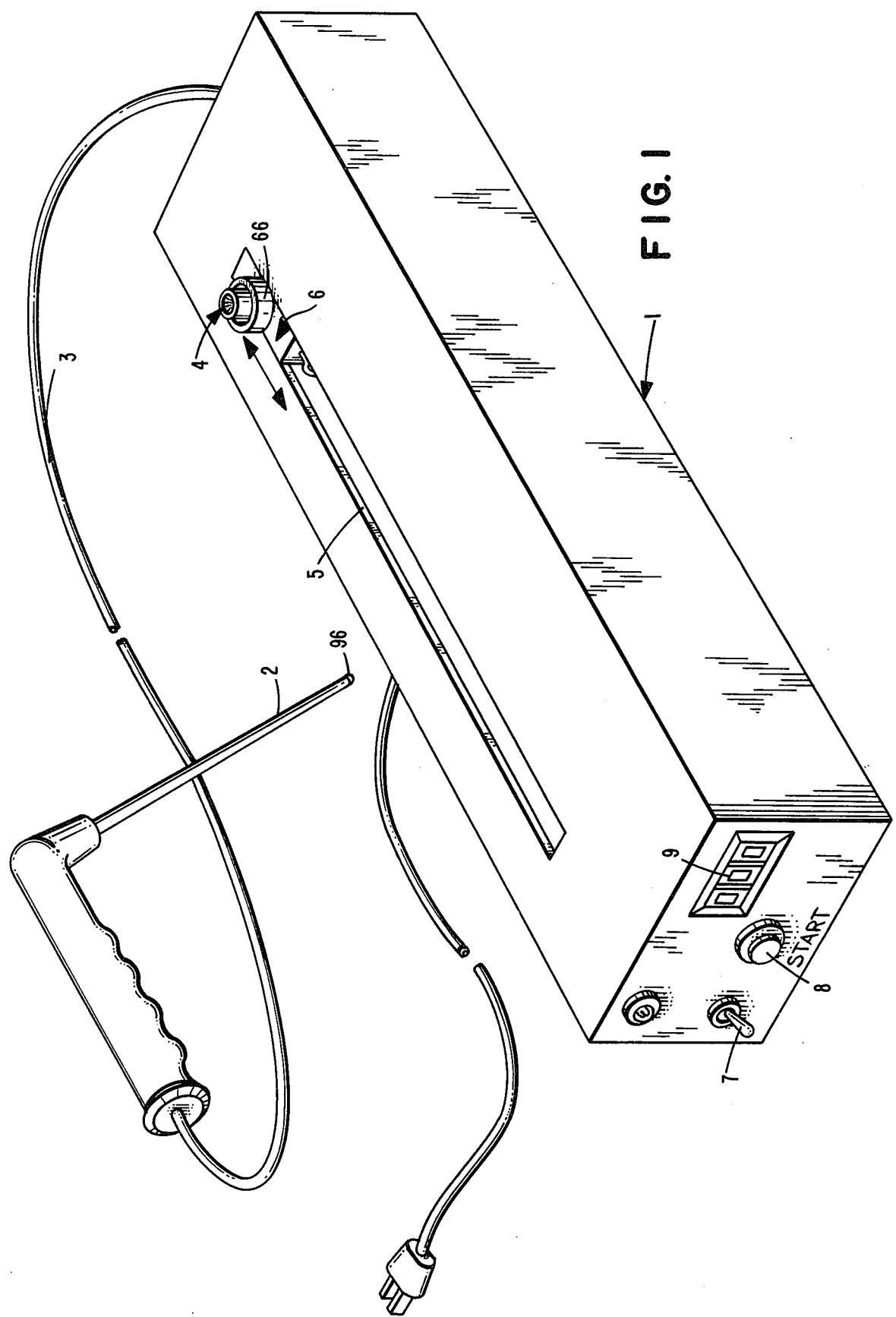
FIG. 1 is a perspective view of the small-motion test device.
Figure 5:
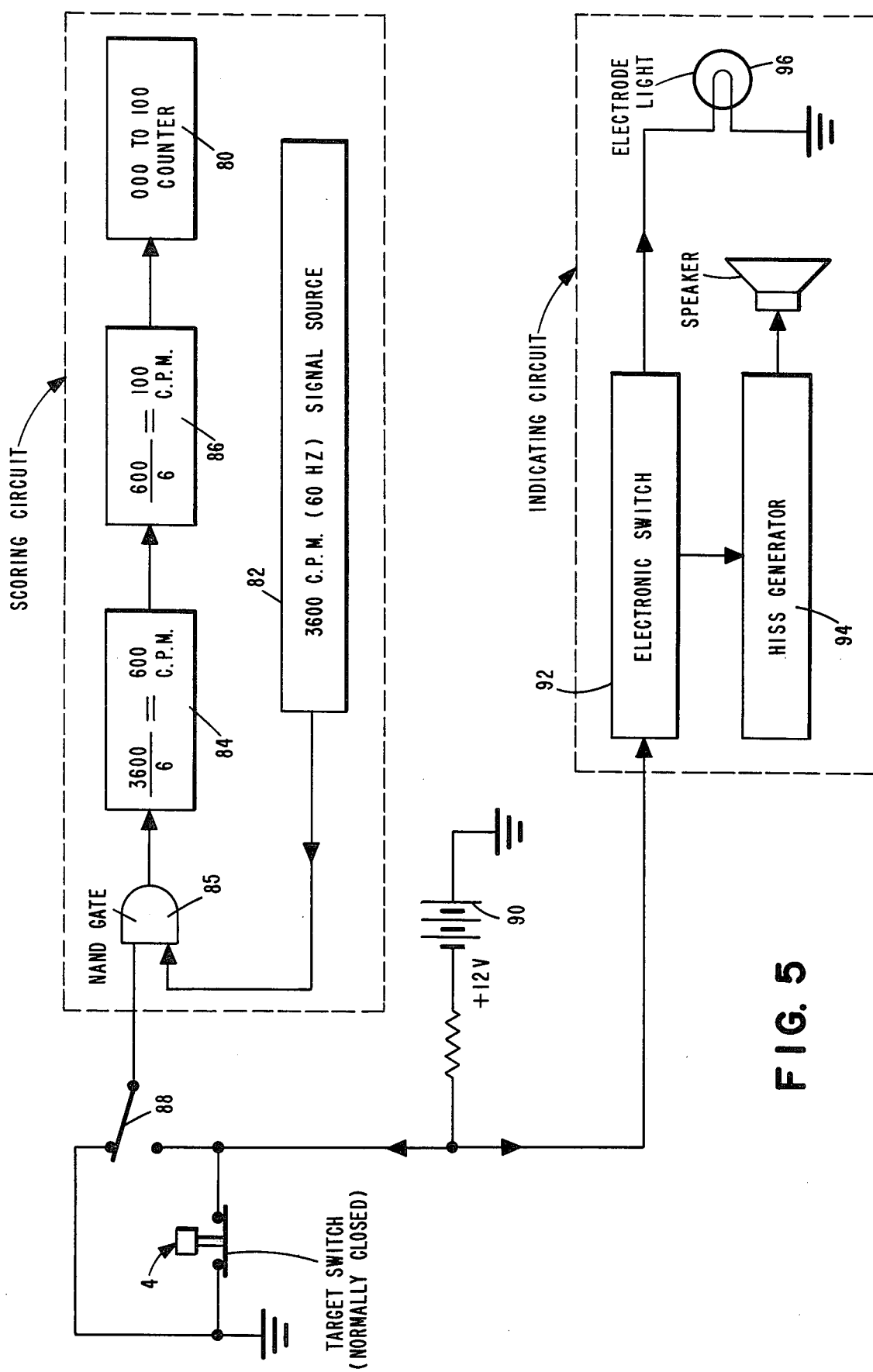
FIG. 5 is a diagram of the electronic circuit of the small-motion tester.

Referring to FIG. 1 of the drawings, the cabinet 1 contains all the operating parts of the small-motion test device with the exception of the test-subject-manipulated wand 2 that is connected electrically by cord 3 to the cabinet. This and other electrical connections of significance are shown in detail schematically at FIG. 5 and described below.

The target 4 travels in slot 5 in the top of the cabinet and is drawn along track 25 located inside the cabinet. Target 4 is carried on carriage 6 which travels along track 25. An on-off switch 7 is provided at the operator end of the cabinet, and a start button 8 for starting the travel of the target from one end of the track 5 to the other is also located at this end. A score indicating unit 9 visible only to the operator and not to the test subject also appears at the end of the cabinet. If desired, an optional practice switch and practice score indicator may also be mounted on the cabinet with an extra start button mounted in the handle of the wand holder; the optional switch has two positions; "practice" and "test". The other score indicator is mounted on the top of the cabinet in a position visible to the test subject. With the switch in the "practice" position, provision is thereby made for a student to improve his manipulative skill by executing repeated test runs in series, with his scores easily visible to him. In testing naive subjects, the optional switch would be moved to the "test" position and the test subject score counter would remain blank. The manner in which a score is accumulated is explained in detail below.

FIG. 2 shows the target 4 driven along the track 25 by a flexible steel wire 14 hooked to each end of the carriage 6 and looped around an idler wheel 15 and drive wheel 16A driven by a combination drive motor and electric clutch 16. The synchronous gear motor 16 is stopped by end-stop limit switch 17. The flexible stainless wire drive belt is joined at its ends by a tension coil spring 18 and an insulating link 19. The motor 16 and idler pully wheel 15 are supported inside the cabinet by suitable structures such as vertical longitudinal wall 28.

Carriage 6 is supported by track 25 which is supported beneath the top wall of cabinet 1 by angle brackets 26. Track 25 is comprised of two opposing C-channels 27 spaced apart to receive the carriage therebetween, as seen in FIG. 4.

Carriage 6 is provided with track engaging shoes 29 attached to the ends of the control insulating body block 7 by screws 31.

FIG. 3 and 4 show the combination of target and switch are the means for defining the envelope of freedom of movement of the target used in the small-motion test. The target piece 4 preferably includes a target button 30 having a conical depression 32 for receiving the tip of the wand; the depression or equivalent means for maintaining contact between wand and target is necessary as the test subject must affirmatively position, by active physical control, the target button 30 within its defined envelope of freedom of movement throughout the test. The envelope of freedom of movement is defined in its vertical phase by the position of the movable contact stud 35 of switch 36. Contact 35 is secured to operating member 38 which is slidably contained in a vertical bore 39 in block 7. Contact 35 extends at a right angle to the axis of member 38 through a hole 54 in block 7. The vertical position of operating member 38 is controlled by push spring 37 secured to the buttom of target button 32 and which extends down through a bore-hole 40 in stop-member 41. Contact 35 is thereby mechanically directly movable with target 4 via push spring 37.

The critical relationship of the contact 35 and the permanently located wires 42, 43 of switch 36 appears clearly in FIG. 3. The switch 36 defines the envelope of freedom of movement of the target in its vertical phase. The contact 35 electrically connected to wire 43 closes a circuit from wire 50 to wire 52 if it touches any part of loop 47 or wire 42 during the test. This circuit closure prevents further score accumulation, as explained below with reference to FIG. 5. The structural relationship of the wires 42, 43 and contact 35 which moves with vertical movement of the target also appears in FIG. 4. It is important to note that in the applications for which this test and training device is designed, a detectable return pressure by the target against the wand to the hand of the operator must be avoided. (In most actual welding there is no tactile feedback). This is achieved herein especially by the design of spring 43 which provides a very light upward bias, and by weighting of the dummy electrode holder or wand 2.

The envelope of freedom of movement of the target button 30 is defined in its horizontal phase by the relationship of annular shoulder flange 62 surrounding the lower end of target button 30 to the collar 66 of member 41 surrounding button 30. Push spring 37 is a thin spring wire which allows target button 30 to move laterally to contact collar 66 if the wand tip 2 moves it over. FIG. 4 illustrates how horizontal movement of button 30 would short the target to the side of the surrounding collar 66 to define the horizontal phase of the envelope of freedom of target movement. The summing of the score ceases while shoulder 62 is shorted to collar 66. (See explanation of scoring with reference to FIG. 5 below). The collar 66 electrically contacts one side of the switch 36 via solder lug 67 and wire 68. If contact occurs between the shoulder of the target 30 and the collar 66, a closed circuit exists that electrically parallels the action of switch 36; the route of the closed circuit is grounded wire 50 through wire 68 through solder lug 67 through collar 66 through target 30 through push rod 37 through operating member 38 through contact 35 through wire 43 through wire 52. All of these elements are mounted on an insulating block 7 to provide circuit insulation from the track and cabinet.

It is shown above that if the test subject who holds the wand in the target depresses the target too far or allows it to rise too high or moves it too far in any horizontal direction, while it travels down the track, the switch 36 closes or the target shoulder 62 shorts to collar 66 and the count ceases. Considering the electrical arrangement, the spring wire 42 of switch 36 and the collar 66 (FIG. 4) surrounding the target 30 are at ground potential. The spring wire 43 and the contact 35 itself which is mechanically coupled to the target 30 are at switching or floating voltage. The spring 43 is connected to the contact 35 as shown in FIGS. 3 and 4. Spring wire 43 normally biases the target support spring 37 upward via contact 35 and operating element 38 when there is no wand pressure on target button 30. The assembly 30, 35, 37, 38 is forced upward by spring 43 until contact 35 is stopped by the upper edge of hole 54 in block 7. This causes the wire 43 (via contact 35) and wire 42 to short together and hold switch 36 normally closed until the target is properly depressed by the test subject. During the test, when the target is properly located by the test subject, the contact 35 is carried down by element 38 to the midway position of the loop 47 of wire 42, breaking the contact 35, 42. Undue vertical movement re-establishes the contact 35, 42; undue lateral movement of the target 4 causes shorting of the shoulder 62 of the target 4 to the surrounding collar 66. Thus both horizontal and vertical envelopes of freedom of movement are defined.

Figure 6:
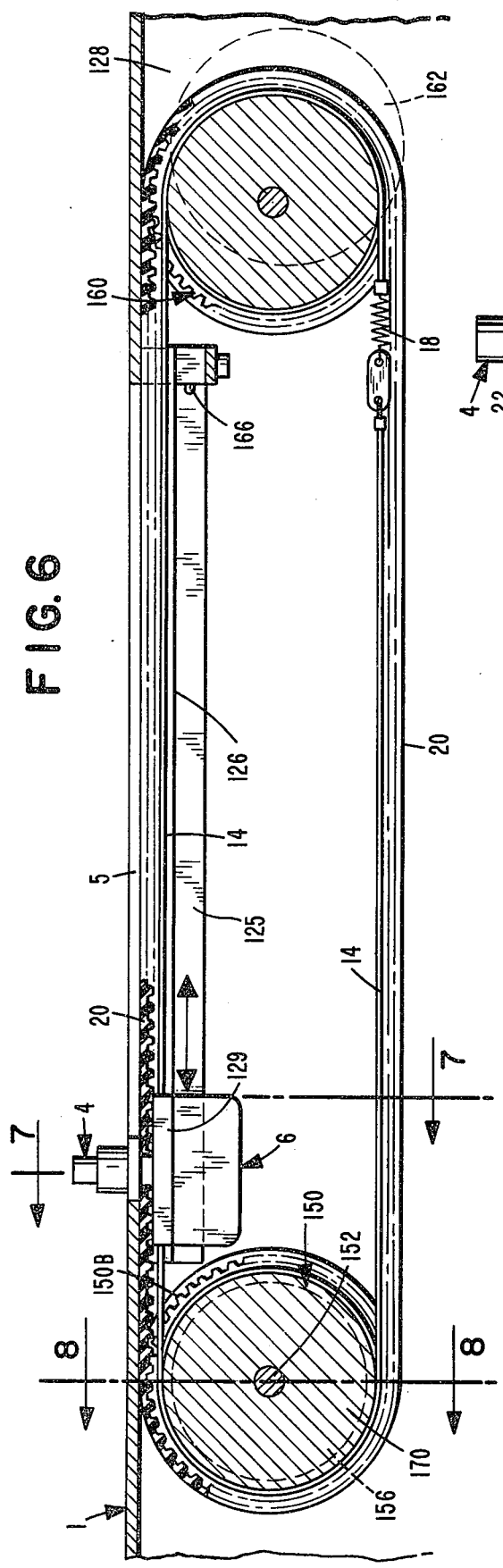
FIG. 6 is a longitudinal sectional view of an alternative embodiment of the features shown in FIG. 2.
Figure 7:
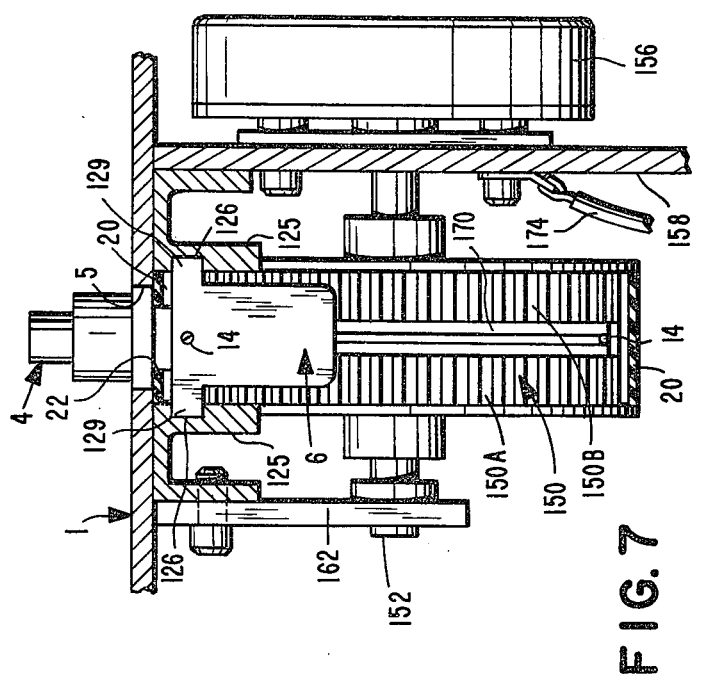
FIG. 7 is a sectional view of the target and return spring taken along the line 7—7 of FIG. 6.
Figure 8:
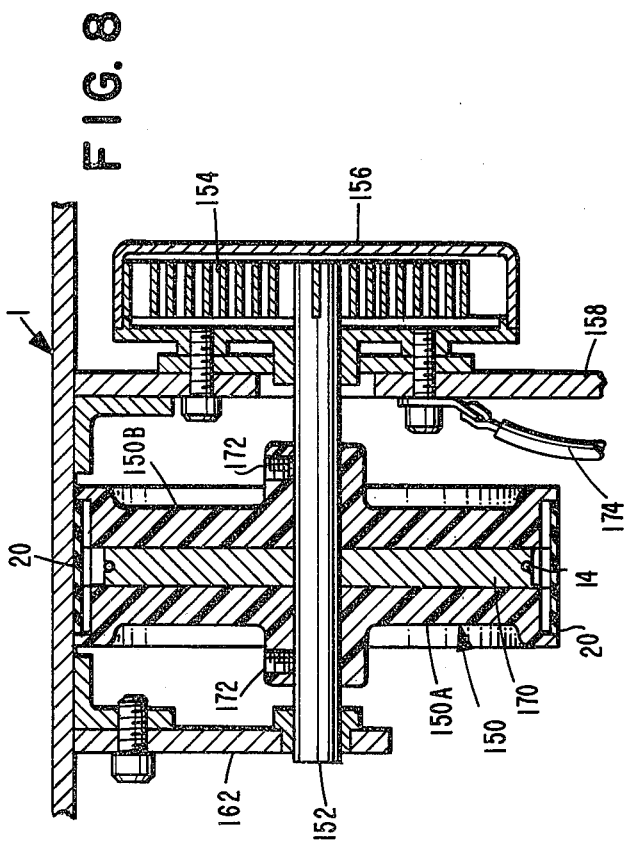
FIG. 8 is a sectional view of the idler wheel and return spring taken on the line 8—8 of FIG. 6.

A preferred alternative embodiment is shown in FIGS. 6–8. In this embodiment, the carriage 6 is held in and moved by a timing belt 20 trained about drive gear 160 at one end of slot 5 and idler gear 150 at the other end thereof. Gear 160 is driven by motor 162. Idler gear 150 is drivingly secured to an axle 152, one end of which is drivingly secured to the inner end of a spiral clock spring 154. Spring 154 is enclosed in a housing 156 attached to a frame member 158. The other end of shaft 152 is journaled in frame member 162.

As carriage 6 is pulled to the right as seen in FIG. 6, spring 154 is wound up. When carriage 6 contacts switch 166, motor 162 is de-energized, allowing carriage 6 and target 4 to be returned to the starting position by the energy stored in spring 154.

In the embodiment shown in FIGS. 2–4, it was necessary to return the target to its starting position by hand.

The action of spring 154 may be damped by filling the housing 156 with a high viscosity fluid.

The target 4 is connected to carriage 6 through a hole 22 in gear belt 20. The belt 20 is held against the bottom edges of the slot 5, thus concealing the interior of the cabinet and preventing the entrance of dust and dirt.

Carriage 6 in this embodiment is provided with lateral flanges 129 which are slidably received in opposing grooves 126 in track members 125. Wire 14 is secured to the front and rear of the carriage as in the first embodiment. Details of the switching mechanism are the same and are omitted in FIGS. 6–8 for simplicity.

Gears 150 and 160 are similar in construction, so only gear 150 will be described in detail:

Gear 150 comprises equal halves 150A, 150B of a flanged, plastic timing belt gear separated by an electrically conductive pulley wheel 170 for entraining wire 14 under belt 20. Gear halves 150A, 150B are secured to shaft 152 by set screws 172. Pulley wheel 170 is secured to both gear halves by cement or the like.

Electrical energy is conducted to wire 14 by conductor 174 electrically connected through spring housing 156, shaft 152 and pulley wheel 170. Shaft 152 is journaled in frame member 162 which together with member 158 are of insulating material so that spring 154, housing 156, axle 152, and pulley wheel 170 remain above ground at switching voltage.

The operation of the target drive is such that when the start button 8 is depressed, the target 4 begins to move from its initial position at the left end of the track, and continues to move at the uniform rate until it stops at the right end of the track. In an exemplary timing/scoring situation, the movement of the target from one end to the other of the 8-inch track takes exactly one minute. The significance of this one minute is apparent from the scoring circuitry shown in FIG. 5 which includes a digital counter 80 reading from 000 to 100, driven by 3600 cycles per minute generator 82 via dividers 84 and 86. Gate 85 is opened by signals received from a voltage source 90 when the button switch 36, the target shoulder 62 to collar 66 switch, and a relay switch 88 all are open. Relay switch 88 is provided to prevent any score from accumulating except when the target drive is running. When the target 4 is set moving on a run, the relay switch 88 contacts open and count may accumulate because of the then availability of signal source voltage 90. This voltage is shorted to ground except when the normally closed target switch is opened by proper positioning of the target in its envelope of freedom of movement. If the target is moved outside the envelope boundaries, the switch closes and the counter stops, indicating that the target is outside its defined envelope of freedom of movement. Thus the counter displays at the end of the run, in 100th's of a minute, the length of time that the target button 30 was maintained in its position within its envelope of freedom of movement during a run of the target over the full 8-inch track. The numerical score between 000 and 100 may also be interpreted as the percentage of the run that the target was held in the proper position. An electronic switch 92 and hiss generator 94 are also provided as shown so that whenever during a run the target switch opens, and is maintained open, a white noise hiss is heard. This feature is included because the device is especially useful as a welding aptitude test and training device. The hiss simulates the sound of proper welding. During successful welding a light also appears at the end of the dummy electrode. These are intended as audible and visible signs to the test subject that he is successfully scoring on the device; such signs are necessary to provide correction signal stimuli to the subject.

A word is in order on the structure of the wand itself. As a preferred embodiment of this device is as a welding training device, in weight, size, shape and appearance the electrode holder was designed as approximating a real electrode holder as presently used in shielded metal arc welding. In its head, at the end of the dummy electrode, is an incandescent light bulb 96. The dummy electrode itself may preferably be made of clear plastic or fiberoptics glass wrapped with reflective aluminum foil and covered with black shrink tubing. When the light in the head of the dummy electrode holder comes on, the clear lower tip of the electrode glows brightly. In carrying out a typical test, the test subject is told to use the tip of the wand to control the position of the target switch as the target moves through a run. Typically, the subject may be allowed to learn the envelope of freedom of movement of the target switch while the target is stationary. The system is designed so that the light and hissing sound may operate while the target is stationary, although no score is summed on the counter. The tester having explained the goals and allowed the test subject to familiarize himself with the equipment, then begins a series of runs by depressing his own start button. At the end of each run the score may be recorded using the counter which displays the run total to the test giver.

Other variations and modifications of this system may be made without departing from the spirit and scope of this invention whose limits are defined only by the appended claims.

I claim:

1. A small-motion test device for testing the hand-eye coordination, correction reflex, and small-motion muscle control of a test subject comprising
    a target
    means for moving said target along a path at a predetermined rate,
    switch means coupled to said target for defining boundaries of a multi-dimensional envelope of freedom of movement of said target,
    a wand controlled by said test subject to affirmatively position said target within the boundaries of said envelope of freedom of movement during travel of said target along said path, and
    means responsive to said switch means for indicating the location of said target within said envelope of freedom of movement.

2. A test device as claimed in claim 1 wherein said switch means comprises a collar surrounding said target,
    said target being movable by said wand to contact said collar,
    said target and said collar comprising a first pair of related contact elements included in said switch means for establishing a signal indication to said indicating means, whereby said collar defines the boundaries of said envelope of freedom of movement in one of said dimensions.

3. A test device as claimed in claim 2 wherein said collar is movable with, but normally out of contact with said target along said path.

4. A test device as claimed in claim 2 further comprising
    a support for said target, at least a portion of said support being movable with said target in one of said dimensions,
    a first element of said switch means being carried by said support,
    a second element of said switch means being located relative to said first element so that movement of said target moves said first and second elements in and out of contact to thereby provide corresponding signal indications of the movement of said target within said boundaries to said indicating means, said second element thereby establishing the boundaries of said envelope of freedom of movement in a second one of said dimensions.

5. A test device as claimed in claim 1 wherein said indicating means comprises a counter, and
    means for supplying driving signals to said counter at a predetermined rate related to the rate of movement of said target along said path
    said switch means being interposed between said driving means and said counter, said switch means controlling the supply of said driving signals to said counter as a function of the location of said target within the boundaries of said envelope of freedom of movement.

6. A test device as claimed in claim 1 wherein said test device comprises a welding training simulation device,
    said target simulating a molten weld puddle,
    said wand simulating an electrode
    said predetermined rate of movement of the target simulating the rate at which a real weld bead is made
    said boundaries of said envelope of freedom of movement of said target establishing the limits of movement of a tip of said electrode within which a successful simulated weld is accomplished.

7. A training device as claimed in claim 6 wherein said indicating means further includes audible and visible indicators responsive to said switch means for indicating the location of said target within said envelope of freedom of movement, said audible indicator portion simulating the sound of said welding.

8. A device as claimed in claim 2 wherein a tip of said wand distal from a portion of said wand held by said test subject is in physical contact with said target to control the location thereof.

9. A method of testing the small-motion muscle control, hand-eye coordination, and correction reflex of a test subject comprising
    moving a target along a path at a predetermined rate,
    defining the boundaries of a multidimensional envelope of freedom of movement of said target by electro-mechanical switch means,
    providing a wand to said test subject, said wand being used by said test subject to controllably position said target within said boundaries of said envelope of freedom of movement through movement of said target along said track,
    the location of said target within said envelope being indicated by indicating means responsive to said switch means.

10. A test device as claimed in claim 9 wherein said test device comprises a welding training simulation device,
    said target simulating a molten weld puddle,
    said wand simulating a welding electrode,
    said boundaries of said envelope of freedom of movement of said target establishing the limits of movement of a tip of said electrode within which a successful simulated weld is accomplished.

* * * * *